United States Patent [19]

Yamada et al.

[11] Patent Number: 5,276,138
[45] Date of Patent: Jan. 4, 1994

[54] PROCESS FOR SOLUBILIZING ANIMAL HAIR

[75] Inventors: Masaru Yamada; Satoshi Narita, both of Tsu; Takashi Kondo, Kyoto; Masaharu Nojima, Tsu; Ryohei Yamamoto, Neyagawa; Toyokazu Nishino, Neyagawa; Chikaaki Sakai, Neyagawa, all of Japan

[73] Assignee: Kurashiki Boseki Kabushiki Kaisha, Kurashiki, Japan

[21] Appl. No.: 993,522

[22] Filed: Dec. 16, 1992

Related U.S. Application Data

[63] Continuation of Ser. No. 760,304, Sep. 16, 1991, abandoned.

[30] Foreign Application Priority Data

Sep. 17, 1990 [JP] Japan ................ 2-248456
Jan. 23, 1991 [JP] Japan ................ 3-006242

[51] Int. Cl.$^5$ .............. C07K 3/02; C07K 15/06
[52] U.S. Cl. .................... 530/357; 530/423; 530/842
[58] Field of Search ............ 530/357, 419, 423, 842

[56] References Cited

U.S. PATENT DOCUMENTS

| | | | |
|---|---|---|---|
| 1,727,866 | 9/1929 | Oieterle et al. | 530/357 |
| 2,413,983 | 1/1947 | Lustig et al. | 530/357 |
| 2,622,036 | 12/1952 | Alexander et al. | 530/357 |
| 3,464,825 | 9/1969 | Anker | 530/357 |
| 4,465,664 | 8/1984 | Matsunaga et al. | 424/71 |
| 4,581,148 | 4/1986 | Swanson et al. | 252/8.57 |
| 4,895,722 | 1/1990 | Abe et al. | 424/71 |

FOREIGN PATENT DOCUMENTS

9001023 2/1990 World Int. Prop. O. .

OTHER PUBLICATIONS

Derwent Accession No. 79-41 674, Questel Telesystems (WPIL) Derwent Publications Ltd., Londo & JP-A-79-10 601 (Osaka Soda).

*Primary Examiner*—Jeffrey E. Russel
*Attorney, Agent, or Firm*—Armstrong, Westerman, Hattori, McLeland, & Naughton

[57] ABSTRACT

The present invention provides the process for treating the animal hairs by solubilization wherein the animal hairs can be treated in a short time without any complicated operations and special apparatuses, and the process for recovering the solubilized product of the animal hairs wherein said product can be recovered simply and efficiently from the solution thereof. The former is the process for treating animal hairs by solubilization which comprises solubilizing the animal hairs in a weak alkaline liquid medium in the presence of an oxidizing agent whose concentration is high. The latter is the process for recovering a solubilized product of animal hairs which comprises admixing a solution of said product with an organic acid or an aqueous solution thereof to precipitate said product.

3 Claims, 1 Drawing Sheet

PROCESS FOR SOLUBILIZING ANIMAL HAIR

This application is a continuation of application Ser. No. 760,304 filed Sep. 16, 1991, now abandoned.

FIELD OF THE INVENTION

The present invention relates to a process for treating animal hairs by solubilization and a process for recovering the solubilized animal hairs.

BACKGROUND OF THE INVENTION

Nowadays, animal hairs focus the spotlight of attention upon the use as a high functional material in the various fields in addition to their rightful use for clothing. For example, the animal hairs have been employed as a trapping agent for heavy metals, an additive for cosmetic and food, a hair tonic, an improver for clothing, an antithrombotic and the like. More extensive uses of the animal hairs have been expected.

For the aforementioned uses as the functional material, fibriform animal hairs must be subjected to pulverization or solubilization because they are unsuitable in themselves.

As a process for pulverizing the fibriform animal hairs, a mechanical pulverization method of the animal hairs themselves, a pulverization method of the pretreated animal hairs with reducing agent, a pulverization method of the frozen animal hairs and the like are exemplified. In these methods, however, a large-scale pulverization apparatus is necessary, sizes of the particulate animal hairs prepared are restricted and complete pulverization of the animal hairs is extremely difficult.

As a process for solubilizing the fibriform animal hairs, the following methods of from (i) to (iii) are exemplified:

(i) A method of extracting protein components after solubilizing the animal hairs by cutting disulfide bond thereof with reducing agent.
(ii) A method of solubilizing the pretreated animal hairs with oxidizing agent in an alkaline solution.
(iii) A method of solubilizing the animal hairs by introducing a hydrophilic group thereinto.

As regards the method (i), use of a solubilizing agent and fairly long solubilization time are necessary because of low solubility of the animal hairs and not only long time is necessary to separate protein gel obtained by dialysis or gel filtration under acidic condition from aqueous phase but also a conservative problem that thiol group of the separated protein gel is reoxidized is brought about because hydrophilicity of the protein gel is considerably high. Concerning the method (ii), it takes long time to solubilize the animal hairs and not only considerable amounts of insoluble animal hairs remain but also long time is necessary to extract the protein. With respect to the method (iii), although solubilization time is relatively short, denaturation of the obtained protein comes into question because said protein is chemically modified by hydrophilic groups.

In connection with the process for solubilizing the animal hairs, a recovery method of the solubilized product of the animal hairs, becomes a subject of discussion. As the recovering method of the solubilized product of the animal hairs, the following methods of (a) and (b) are suggested:

(a) A method of recovering the solubilized product as a gel by adding a volatile inorganic acid such as hydrochloric acid, nitric acid, and the like to the solution of the solubilized product of the animal hairs.

(b) A method of recovering the solubilized product as a water insoluble product by subjecting the solution of the solubilized product of the animal hairs to a crosslinking treatment.

With respect to the method (a), there is a drawback that a filtration treatment becomes very difficult because a filter is blocked by a gelled protein. As regards the method (b), there is a disadvantage that a use of the collected product is excessively restricted because the animal hair protein is chemically modified completely by a crosslinking agent.

Although a flocky precipitate can be obtained in the method (a) when the pH of the solution is lowered by increasing a concentration of the inorganic acid, a color of the precipitate is turned to brown when the precipitate is subjected to a drying treatment in an insufficiently dehydrated state because dehydration efficiency of the precipitate is extremely low, said low efficiency of the dehydration being attributable to the occluded water within the precipitate.

In addition to the abovementioned methods, it is known that the gelled protein obtained by the method (a) may be dehydrated by washing said protein with a volatile polar solvent such as alcohol, acetone and the like. However, it is hard to supply the solubilized product of the animal hairs at a low price because a large quantity of the solvent which is relatively expensive must be used and, therefore, it is necessary to utilize an apparatus for recovering the used solvent.

OBJECTS OF THE INVENTION

One object of the present invention is to solve the aforementioned problems concerning the process for treating the animal hairs by pulverization or solubilization and to provide a process for treating the animal hairs by solubilization wherein the animal hairs can be treated in a short time without complicated operations and special apparatus.

The other object of the present invention is to solve the aforesaid problems concerning the process for recovering the solubilized product of the animal hairs and to provide a process for recovering said product wherein said product can be recovered simply and efficiently from the solution of the product.

SUMMARY OF THE INVENTION

According to one aspect of the present invention, a process for treating animal hairs by solubilization which comprises solubilizing the animal hairs in a weak alkaline liquid medium in the presence of an oxidizing agent whose concentration is high is provided.

According to the other aspect of the present invention, a process for recovering a solubilized product with an organic acid or an aqueous solution thereof to precipitate said product is provided.

DETAILED DESCRIPTION OF THE INVENTION

Figure 1:
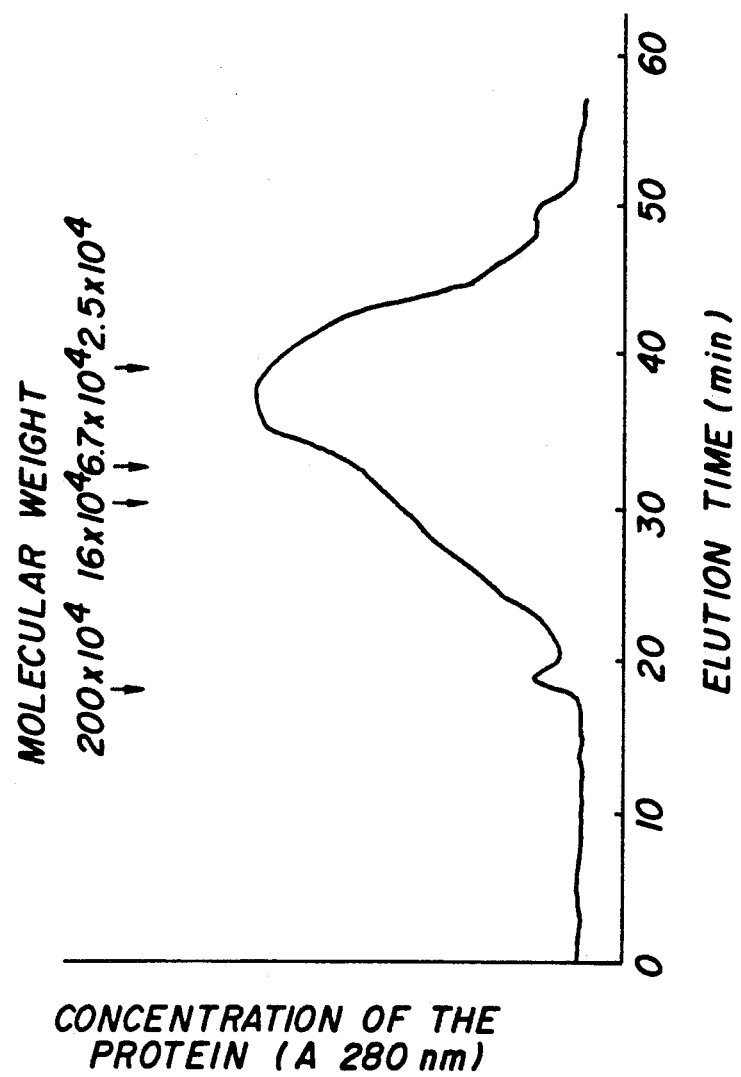
FIG. 1 is the chromatogram of the wool powder prepared in the following Example 1.

As the animal hairs which may be used in the present invention, wool, which is a typical one, alpaca, mohair, angora, kashmir, feather and the like are exemplified. However, the animal hairs which can be employed in the present invention are not restricted to these animal hairs.

As the liquid medium which may be used in the present invention, water, alcohols such as methanol, ethanol and propanol and the like are exemplified. Mixtures of two or more of the liquid media can optionally be used.

As a pH adjuster which makes the liquid media weakly alkaline, ammonia, amines, alkali metal hydroxide, alkali metal carbonate and the like are exemplified. The pH adjuster may suitably be selected depending on the kinds of the liquid medium for solubilizing the animal hairs and the oxidizing agents and the like.

Under normal conditions, the pH of the liquid medium is 4–12, preferably 8–9. When the pH of the liquid medium is more than 11, peptide bonds of main chain of the protein are cut excessively and the protein is decomposed into oligopeptides. As a result of the excessive decomposition of the protein, yield of the solubilized product of the animal hairs as a protein is lowered. If the pH of the liquid medium is less than 7, the oxidizing agents do not function well. For example, a decomposition reaction of hydrogen peroxide which is the most preferable oxidizing agent becomes hard to proceed, a time for solubilizing the animal hairs becomes longer because of unsufficient exothermic reaction for which heating, is necessary, and an addition of an acceleration agent for decomposing hydrogen peroxide such as iron ion, copper ion and the like may be required as the occasion may demand.

As the oxidizing agents which may be used in the present invention, peroxides such as hydrogen peroxide, peracetic acid, performic acid and the like are exemplified. However, hydrogen peroxide is the most preferable oxidizing.,agent for the present invention because not only is it inexpensive and convenient to handle but also a post-treatment of the solubilized product of the animal hairs is easy and no harmful ingredients remains in said solubilized product when hydrogen peroxide is used.

Under normal condition, concentrations of the oxidizing agents are more than 20% by weight, preferably 25–35% by weight. When the concentrations of the oxidizing agents are less than 10%, an expected object of the present invention cannot be achieved as a general rule.

Although a solubilization mechanism of the animal hairs according to the present invention is not completely elucidated, the following mechanism is supposed. Disulfide bonds of keratin of the animal hairs are cleaved by an action of the oxidizing agent on said bonds and two cysteic acid residues are produced from one cystine residue. Peptide bonds of main chain which are adjacent to said disulfide bonds are cut by heat of said cleavage reaction and on electrophilic action of side chain of the produced cysteic acid. The animal hairs can be solubilized in a keratose form through these reactions. The solution obtained is named "keratin solution."

The time for solubilizing the animal hairs is about 0.1–1.0 hour as a general rule although a solubility of the animal hairs depends on a kind and a concentration of the oxidizing agent, a kind of the liquid medium for solubilization and the like. For example, when the animal hairs are immersed in 35% by weight aqueous solution of hydrogen peroxide whose pH is adjusted to about 8 with ammonia water, temperature of the aqueous solution is elevated to about 100° C. spontaneously and the animal hairs are solubilized completely without remaining insoluble matter within an hour.

The keratin solution prepared by the aforementioned solubilization treatment is relatively stable and is well preserved for several weeks under the normal temperature.

In general, the pH of the aforesaid keratin solution is 4.5–6.5. The keratin solution can be utilized as a reaction component with which various mononers having high molecular weight such as acrylic copolymers are reacted. For this purpose, the keratin solution may be used directly or after the pH thereof is suitably adjusted. The keratin solution to which an enzyme for decomposing hydrogen peroxide is added can be used as a blending ingredient of a cosmetic such as manicure, hairdressing and the like.

Gelled precipitate prepared by adding an acid such as acetic acid and the like to the keratin solution can be used as an adsorbent for metal ions. Powder prepared by treating said gelled precipitate with a polar solvent such as alcohols, acetone and the like can be utilized not only as a blending ingredient for a cosmetic but also as a blending component for various industrial treating agents such as paints and the like. Furthermore, a film obtained by a film-forming treatment of the keratin solution (e.g. a blending of the keratin solution with polyamide prepolymers) can be used as an adsorptive functional film and the like.

As previously stated, the present invention relates also to the process for recovering the solubilized product of the animal hairs which comprises admixing the solution of said product with an organic acid or an aqueous solution thereof to precipitate said product.

The term "an organic acid" used in the present specification includes also salts of organic acids as well as acid anhydrides.

As the organic acids which may be used in the present invention, acetic acid, oxalic acid, citric acid, succinic acid, tartaric acid, propionic acid, p-toluenesulfonic acid and the like are exemplified. Citric acid, succinic acid and tartaric acid are preferable in particular. As the acid anhydrides, acetic anhydride, phthalic anhydride, benzoic anhydride and the like are exemplified. As the salts, alkali metal salts, alkaline earth metal salts or amine salts of the aforesaid organic acids and the like are exemplified. Sodium salts, potassium salts and lithium salts are preferred. Although the amounts of the organic acids to be employed depend on a kind of the organic acids, concentration of the solubilized product of the animal hairs and so forth and are not restricted, they, should usually be 0.1–10%, preferably 1–5% by weight as a final concentration. When the aqueous solutions of the organic acids are used, concentrations of the aqueous solutions are so adjusted that the final concentrations of the organic acids become 0.1–10% by weight. Mixtures of two or more of the organic acids may optionally be employed.

Under normal conditions, the pH of the mixed system of the solution of the solubilized product of the animal hairs and the organic acid may be adjusted less than about 4.5, preferably 1–4. If the pH of the mixed system is more than 4.5, the solubilized product of the animal hairs becomes hard to precipitate. Depending on the kinds of the organic acids to be employed, the pH of the mixed system cannot be adjusted within the above range. In such a case, it is necessary to adjust the pH of the mixed system by using other suitable organic acid or inorganic acids (e.g. hydrochloric acid, sulfuric acid, phosphoric acid and the like). For example, when citric acid or a buffer solution containing citric acid such as Kolthoff buffer solution or McIlvaine buffer solution is added to an aqueous solution of the solubilized product of the animal hairs (pH 5.8), the pH of the mixed system becomes approximately 3.6 and the solubilized product is precipitated as a fine white solid. However, when Walpole buffer solution is added to the aqueous solution of the solubilized product of the animal hairs (pH 5.8), the pH of the mixed system becomes about 5 and no precipitate is formed. In the latter, if the pH of the mixed system is adjusted to approximately 1.7, white precipitate can be obtained.

A temperature of the system at the time of mixing the solubilized product solution of the animal hairs with the organic acids is less than about 40 °C., preferably 4°-35° C. as a general rule. The precipitate obtained by mixing said solubilized product solution and the organic acids can efficiently be recovered by the conventional methods such as filtration, centrifugal separation and the like.

The recovered precipitate can be used without any post-treatment depending on the usage. However, the recovered precipitate may be used after removing impurities such as trace amounts of stinking components having low molecular weight, colored substances and the like contained in the solubilized product solution of the animal hairs by washing said precipitate with the aqueous solutions of the organic acids and/or volatile organic solvents such as alcohols, acetone and the like and then drying said washed precipitate.

As a preparation method of the solubilized product solution of the animal hairs which may be employed in the aforementioned process for recovering said solubilized product, the oxidizing decomposition method according to the first aspect of the present invention, an enzymatic method wherein various kinds of enzymes for decomposing proteins which hydrolyze keratin that is a main ingredient of the animal hairs are used, a reducing method wherein reducing agents such as mercaptoethanol, mercaptoethylamine and the like are used, and so forth are exemplified. However, the oxidizing decomposition method is preferred in particular from the aforementioned reasons.

The present invention will be illustrated by the following examples.

EXAMPLES

Example 1

A wool solution (pH 5.8) was prepared by solubilizing 200 g of wool top (merino) in 1000 ml of 35% by weight aqueous hydrogen peroxide solution whose pH was adjusted to 8 with ammonia water. In the process for solubilizing the wool top, drastic decomposition reaction of hydrogen peroxide occurred after 15 minutes from the time of immersing the wool top in the aqueous hydrogen peroxide solution and a temperature of the reaction system was increased to about 100° C. The wool top was solubilized nearly completely during an hour.

The wool solution was allowed to stand for an hour to decrease the temperature of said solution to 40°-50° C. and then subjected to a filtering treatment by means of stainless filter (100 mesh). About 1200 ml of wool suspension was obtained. An amount of an insoluble residue was about 0.5 g.

A gelled precipitate was obtained by decreasing the pH of the wool suspension to about 3 with acetic acid. Ethanol (4000 ml) was added to the gelled precipitate and said mixture was filtered with suction by means of filter paper (5A). The filtered product was washed with acetone several times and then dried at 80° C. About 170 g of wool powder was obtained. Fine wool powder whose grain size is approximately 1-10 $\mu$ was prepared by pulverizing the wool powder by means of mortar.

Amino acid compositions of the fine wool powder and the material thereof are shown in Table 1. As apparent from Table 1, there is marked difference between the cystine content of the fine wool powder and that of the wool.

In order to estimate the molecular weights of the fine wool powder, said powder was solubilized in 0.1M boric acid buffer (pH 9) and the solution of the powder was eluted on Superose 12 HR 10/30 column which is commercially available from Farmasia Fine Chemical Inc. The obtained chromatogram is shown in FIG. 1.

Example 2

When 100 ml of the wool solution prepared in Example 1 was mixed with a 200ml aqueous solution (pH 2.3) containing citric acid (4 g), wool protein was precipitated instantaneously and fine white precipitate was obtained after 2 hours. The pH of the supernatant solution was 3.6. The white precipitate was filtered with suction by means of filter paper (No. 2). The filtration was completed in 2 minutes. The white precipitate was washed with the aqueous solution of citric acid (100 ml) twice and about 40 g of the obtained precipitate was subjected to a drying treatment under reduced pressure. The wool protein was obtained as a citrine solid (15 g).

TABLE 1

| amino acids | amino acid composition (mole %) | |
|---|---|---|
| | wool | fine wool powder |
| asparaginic acid | 6.9 | 8.7 |
| threonine | 5.3 | 5.3 |
| serine | 7.5 | 7.8 |
| glutamic acid | 12.5 | 14.1 |
| glycine | 9.1 | 8.7 |
| alanine | 5.9 | 6.1 |
| ½ cystine | 7.9 | — |
| valine | 6.7 | 6.8 |
| methionine | 0.5 | 0.2 |
| isoleucine | 3.4 | 3.6 |
| leucine | 8.3 | 8.4 |
| tyrosine | 3.6 | 2.7 |
| phenylalanine | 3.1 | 2.5 |
| lysine | 3.1 | 2.1 |
| histidine | 0.9 | 0.4 |
| arginine | 7.1 | 7.4 |
| proline | 8.2 | 7.1 |
| cysteic acid | — | 8.1 |

In order to determine a grain, size distribution, the citrine solid was pulverized for about 2 hours by means of ball mill. The grain size distribution of the pulverized solid was measured by means of Shimazu laser diffraction type apparatus for measuring grain size distribution. The wool protein powder has the grain size distribution wherein the powder whose grain size is 1.00-4.80 $\mu$m occupies 90% of the whole based on the length or the powder whose grain size is 9.00-59.00 $\mu$m occupies 65% of the whole based on the volume.

Example 3

The white precipitate of the wool protein was prepared according to the same procedure as that of Example 2 except for using Kolthoff buffer (200 ml) whose pH was adjusted to 2.94 with 0.3M aqueous solution of potassium dihydrogen citrate and 0.3M aqueous solution of citric acid in place of the aqueous solution of citric acid. The pH of the supernatant solution was 3.51. The white precipitate was filtered. The filtration was completed in 2 minutes. The white precipitate was washed with the Kelthoff buffer (100 ml) twice and about 40 g of the obtained precipitate was subjected to a drying treatment under reduced pressure. The wool protein was obtained as a citrine solid (15 g).

Example 4

The white precipitate of the wool protein was prepared according to the same procedure as that of Example 2 except for using McIlvaine buffer (200 ml) whose pH was adjusted to 2.84 with 0.6M aqueous solution of disodium hydrogen phosphate and 0.3M aqueous solution of citric acid in place of the aqueous solution, of citric acid. The pH of the supernatant solution was 3.56. The white precipitate was filtered. The filtration was completed in 2 minutes. The white precipitate was washed with the McIlvaine buffer (100 ml) twice and about 40 g of the obtained precipitate was subjected to a drying treatment under reduced pressure. The wool protein was obtained as a citrine solid (15 g).

Example 5

The same procedure as that of Example 2 carried out except for using Walpole buffer (200 ml) whose pH was adjusted to 1.70 with 1M aqueous solution of sodium acetate, 1N hydrochloric acid and water in place of the aqueous solution of citric acid. The pH of the mixed solution was 4.70. After 2 hours, the mixed solution was gelled and no precipitate of protein was formed. However, flocky white precipitate was obtained by adjusting the pH of the liquid mixture to about 1.72 with hydrochloric acid. The obtained white precipitate was filtered. The filtration was completed in 2 minutes. The white precipitate was washed with the Walpole buffer (100 ml) twice and about 45 g of the obtained precipitate was subjected to a drying treatment under reduced pressure. The wool protein was obtained as a citrine solid (15 g).

Example 6

The white precipitate of the wool protein was prepared according to the same procedure as that of Example 2 except for using a solution prepared by solubilizing tartaric acid (4 g) in water (200 ml) in place of the aqueous solution of citric acid. The pH of the supernatant solution was 3.3. The white precipitate was filtered. The filtration was completed in 2 minutes. The white precipitate was washed with the aqueous solution of tartaric acid (100 ml) twice and about 40 g of the obtained precipitate was subjected to a drying treatment under reduced pressure. The wool protein was obtained as a citrine solid (15 g).

According to the present invention of the process for treating the animal hairs by solubilization, the animal hairs can be treated in a short time without complicated operations and special apparatuses. The keratin solution prepared by said process as well as the gelled matters, the powders or the films prepared by water-insolubilizing treatment of said keratin solution can be utilized as, for example, additives for cosmetics and foods, blending components for various industrial treating agents or materials, medical materials and the like.

According to the present invention of the process for recovering the solubilized products of the animal hairs, said solubilized product can be recovered simply and efficiently from the solution of said solubilized products. Therefore, the present invention provides the solubilized products of the animal hairs in large quantities and economically, said solubilized products being used not only as materials for cosmetics and medical supplies but also as industrial materials, blending ingredients for foods and the like.

What is claimed is:

1. A process for solubilizing animal hair which comprises contacting the animal hair in an alkaline liquid medium containing more than 20% by weight of hydrogen peroxide at a pH of 8-9.

2. A process for preparing a keratin solution which comprise solubilizing animal hair by contacting the animal hair in an alkaline liquid medium containing more than 20% by weight of hydrogen peroxide at a pH of 8-9.

3. A process for preparing keratin powder which comprises contacting the animal hair in an alkaline liquid medium containing more than 20% by weight of hydrogen peroxide at a pH of 8-9 to form a keratin solution, acidifying the keratin solution to form a gel, and washing the gel with a polar solvent to form keratin powder.

* * * * *